(12) United States Patent
Takatera

(10) Patent No.: US 11,596,425 B2
(45) Date of Patent: Mar. 7, 2023

(54) BASKET CATHETER, METHOD FOR PRODUCING THE SAME AND MEDICAL TREATMENT INSTRUMENT

(71) Applicant: KANEKA CORPORATION, Osaka (JP)

(72) Inventor: Masayuki Takatera, Settsu (JP)

(73) Assignee: KANEKA CORPORATION, Osaka (JP)

( * ) Notice: Subject to any disclaimer, the term of this patent is extended or adjusted under 35 U.S.C. 154(b) by 423 days.

(21) Appl. No.: 16/628,912

(22) PCT Filed: May 21, 2018

(86) PCT No.: PCT/JP2018/019523
§ 371 (c)(1),
(2) Date: Jan. 6, 2020

(87) PCT Pub. No.: WO2019/039011
PCT Pub. Date: Feb. 28, 2019

(65) Prior Publication Data
US 2020/0121337 A1 Apr. 23, 2020

(30) Foreign Application Priority Data
Aug. 24, 2017 (JP) .............................. JP2017-161611

(51) Int. Cl.
*A61B 17/221* (2006.01)
*A61B 1/00* (2006.01)
(Continued)

(52) U.S. Cl.
CPC ........ *A61B 17/221* (2013.01); *A61B 1/00165* (2013.01); *A61B 17/22031* (2013.01);
(Continued)

(58) Field of Classification Search
CPC .......... A61B 17/221; A61B 17/320725; A61B 2017/2212; A61B 2017/00862;
(Continued)

(56) References Cited

U.S. PATENT DOCUMENTS 6,168,622 B1    1/2001  Mazzocchi et al.
6,605,102 B1    8/2003  Mazzocchi et al.
(Continued)

FOREIGN PATENT DOCUMENTS

CN    102023338 A    4/2011
CN    103826554 A    5/2014
(Continued)

OTHER PUBLICATIONS

International Search Report, issued in PCT/JP2018/019523, PCT/ISA/210, dated Jul. 31, 2018.

*Primary Examiner* — Wade Miles
(74) *Attorney, Agent, or Firm* — Birch, Stewart, Kolasch & Birch, LLP

(57) ABSTRACT

The present invention aims to provide a basket catheter that easily transmits rotational torque on a proximal side to a basket part and can remove a captured foreign matter. The basket catheter (1) has a distal side and a proximal side, has an outer tubular member (2), an inner tubular member (3) disposed in a lumen of the outer tubular member (2) and an expandable basket part (10) disposed on the distal side of the inner tubular member (3) and including elastic wires (15). The inner tubular member (3) includes a hollow coil body (4) formed of a wire wound spirally. In the above basket catheter (1), the elastic wires (15) and the inner tubular member (3) are preferably connected together through a tubular connector (20).

13 Claims, 6 Drawing Sheets

(51) Int. Cl.
    *A61B 17/22*     (2006.01)
    *A61B 17/3203*   (2006.01)
    *A61B 18/26*     (2006.01)
    *A61B 17/00*     (2006.01)
    *A61M 25/00*     (2006.01)

(52) U.S. Cl.
    CPC ......... *A61B 17/32037* (2013.01); *A61B 18/26* (2013.01); *A61B 2017/00526* (2013.01); *A61B 2017/00862* (2013.01); *A61B 2017/22038* (2013.01); *A61B 2017/22051* (2013.01); *A61B 2017/22072* (2013.01); *A61M 2025/0042* (2013.01)

(58) Field of Classification Search
    CPC .......... A61M 25/0133; A61M 25/0138; A61M 25/0141; A61M 25/0023; A61M 2025/0004; A61M 2025/0006; A61F 2/01; A61F 2/0103; A61F 2/0105; A61F 2/0108; A61F 2002/016
    See application file for complete search history.

(56) References Cited

U.S. PATENT DOCUMENTS

| | | |
|---|---|---|
| 2001/0000797 A1 | 5/2001 | Mazzocchi et al. |
| 2002/0062135 A1 | 5/2002 | Mazzocchi et al. |
| 2002/0072765 A1 | 6/2002 | Mazzocchi et al. |
| 2002/0087187 A1 | 7/2002 | Mazzocchi et al. |
| 2002/0095172 A1 | 7/2002 | Mazzocchi et al. |
| 2002/0095173 A1 | 7/2002 | Mazzocchi et al. |
| 2002/0138095 A1 | 9/2002 | Mazzocchi et al. |
| 2002/0169474 A1 | 11/2002 | Kusleika et al. |
| 2004/0006368 A1 | 1/2004 | Mazzocchi et al. |
| 2005/0021076 A1 | 1/2005 | Mazzocchi et al. |
| 2005/0090857 A1 | 4/2005 | Kusleika et al. |
| 2005/0119689 A1 | 6/2005 | Mazzocchi et al. |
| 2005/0119690 A1 | 6/2005 | Mazzocchi et al. |
| 2005/0192623 A1 | 9/2005 | Mazzocchi et al. |
| 2005/0192624 A1 | 9/2005 | Mazzocchi et al. |
| 2005/0203570 A1 | 9/2005 | Mazzocchi et al. |
| 2005/0203571 A1 | 9/2005 | Mazzocchi et al. |
| 2005/0203572 A1 | 9/2005 | Mazzocchi et al. |
| 2005/0203573 A1 | 9/2005 | Mazzocchi et al. |
| 2005/0203574 A1 | 9/2005 | Mazzocchi et al. |
| 2005/0216051 A1 | 9/2005 | Mazzocchi et al. |
| 2005/0216052 A1 | 9/2005 | Mazzocchi et al. |
| 2005/0222606 A1 | 10/2005 | Mazzocchi et al. |
| 2008/0065146 A1 | 3/2008 | Mazzocchi et al. |
| 2008/0065147 A1 | 3/2008 | Mazzocchi et al. |
| 2008/0071308 A1 | 3/2008 | Mazzocchi et al. |
| 2008/0071309 A1 | 3/2008 | Mazzocchi et al. |
| 2008/0125806 A1 | 5/2008 | Mazzocchi et al. |
| 2011/0208234 A1 | 8/2011 | Mazzocchi et al. |
| 2013/0053830 A1 | 2/2013 | Edwards et al. |
| 2014/0142557 A1 | 5/2014 | Kosugi et al. |
| 2015/0306347 A1* | 10/2015 | Yagi .................. A61M 25/0067 604/524 |
| 2016/0045215 A1 | 5/2016 | Edwards et al. |
| 2016/0278805 A1* | 9/2016 | Hatta ............. A61B 17/320725 |
| 2017/0065227 A1* | 3/2017 | Marrs .................... A61B 5/283 |
| 2017/0189056 A1* | 7/2017 | Nakano .......... A61B 17/320758 |
| 2018/0344975 A1 | 12/2018 | Ito |

FOREIGN PATENT DOCUMENTS

| | | |
|---|---|---|
| CN | 103830830 A | 6/2014 |
| JP | 10-504738 A | 5/1998 |
| JP | 2005-21195 A | 1/2005 |
| WO | WO 2017/135131 A1 | 8/2017 |

\* cited by examiner

[FIG. 1]
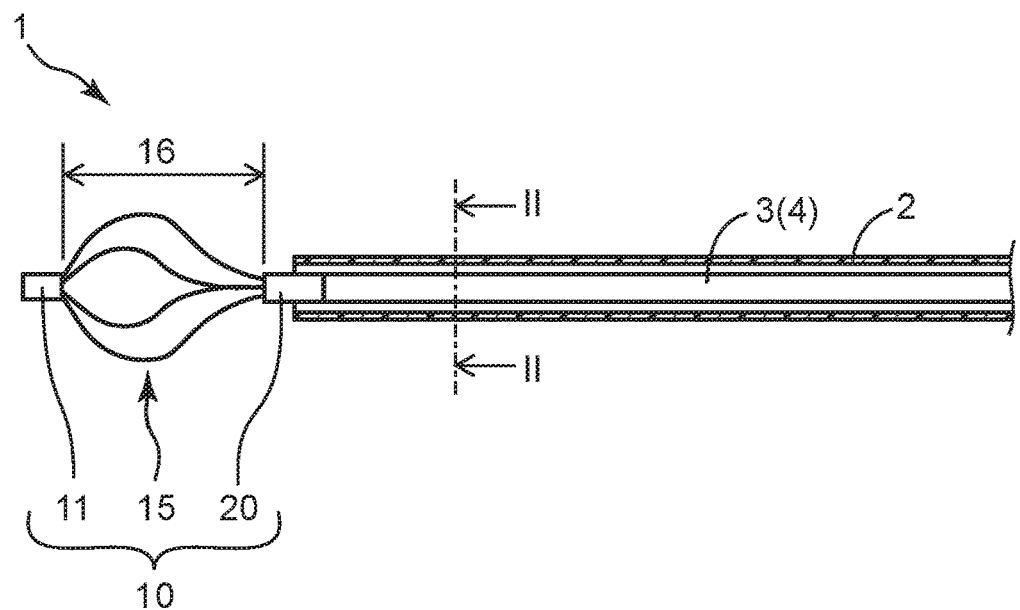
[FIG. 2]
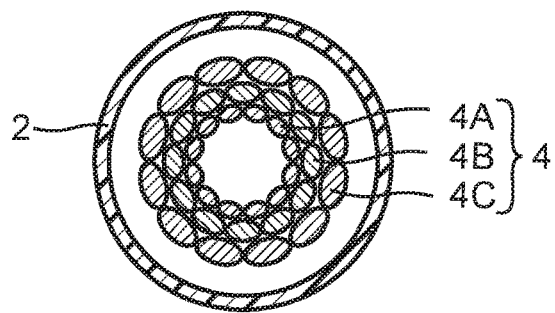
[FIG. 3]
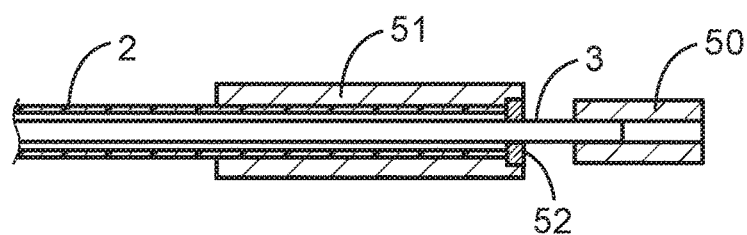

[FIG. 4]
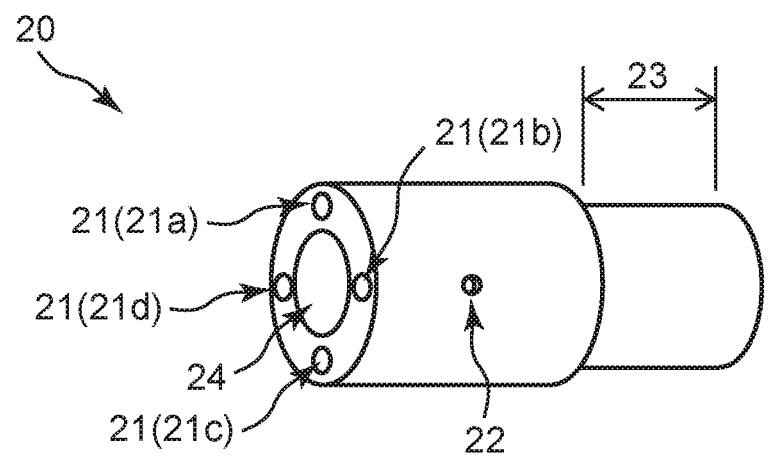
[FIG. 5]
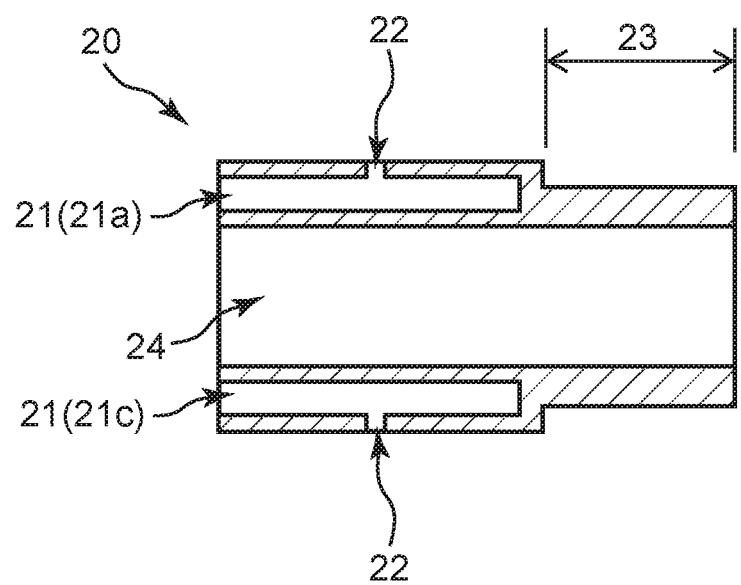

[FIG. 6]
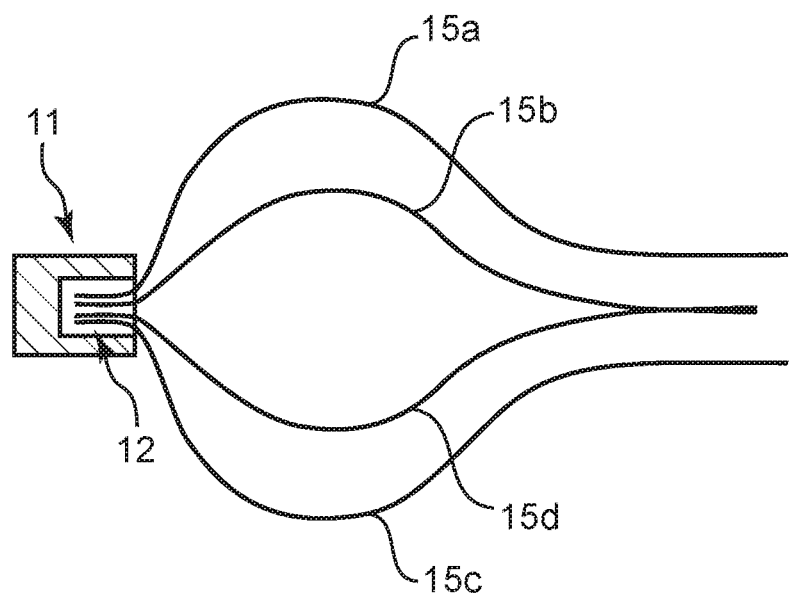
[FIG. 7]
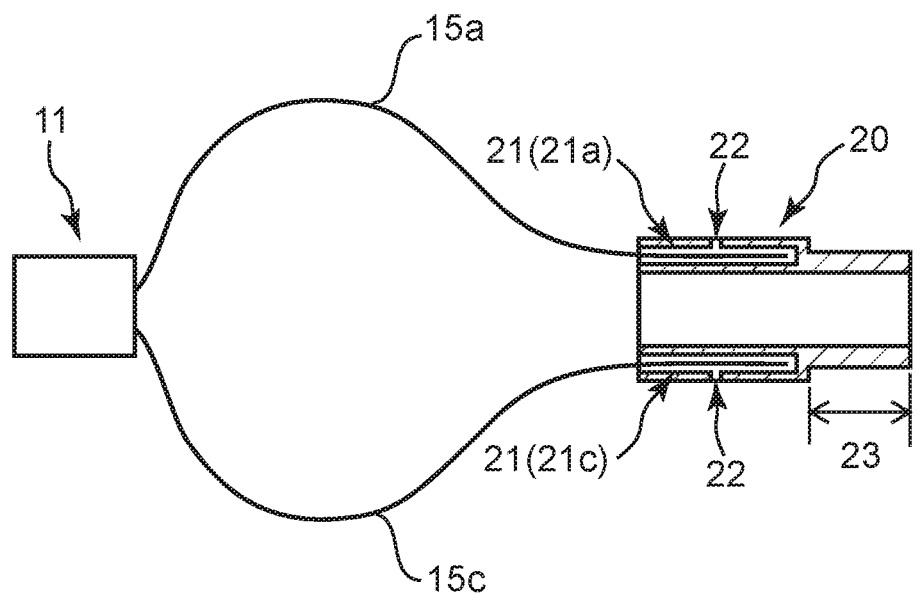

[FIG. 8]
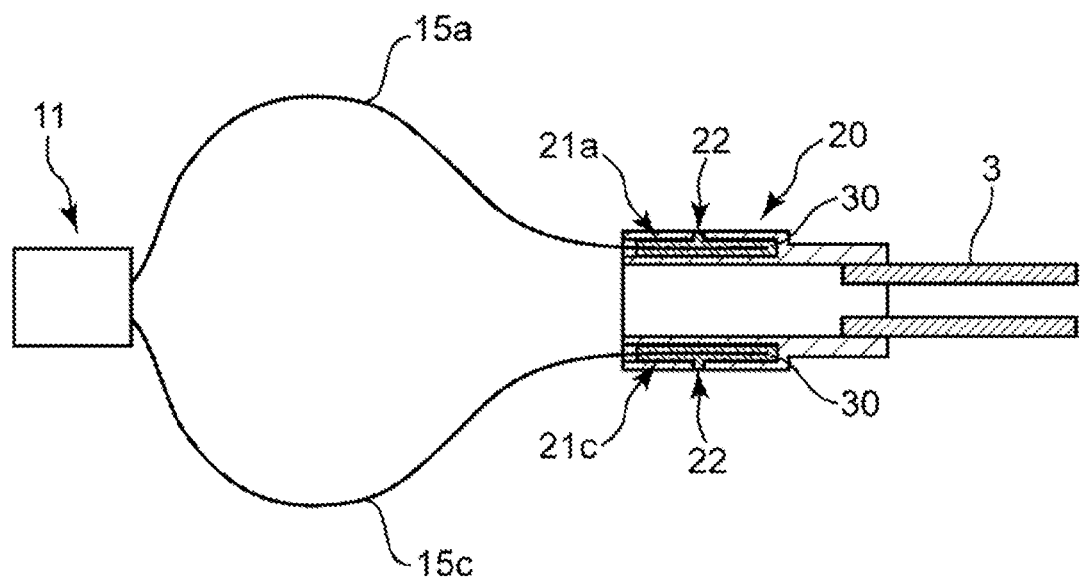
[FIG. 9]
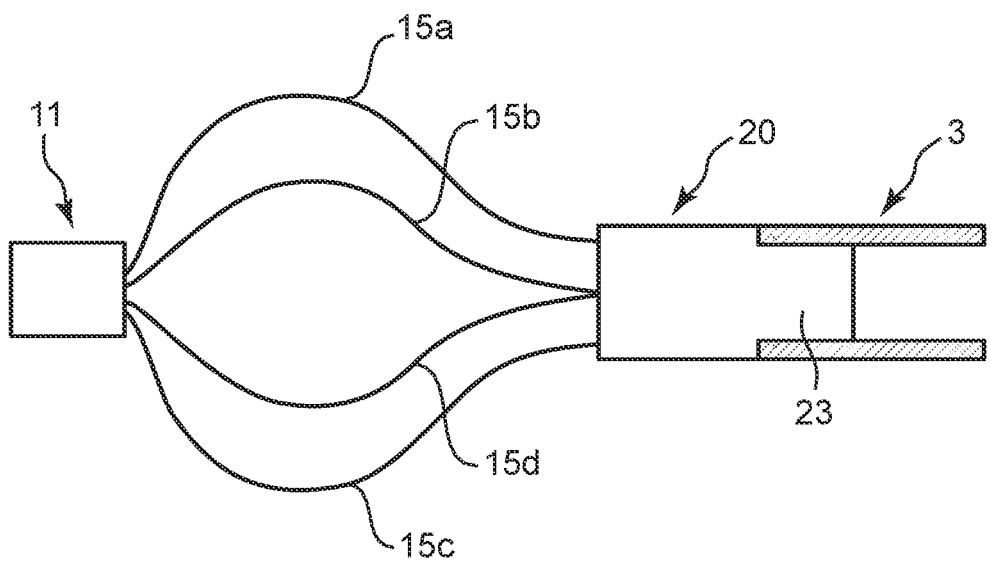

[FIG. 10]
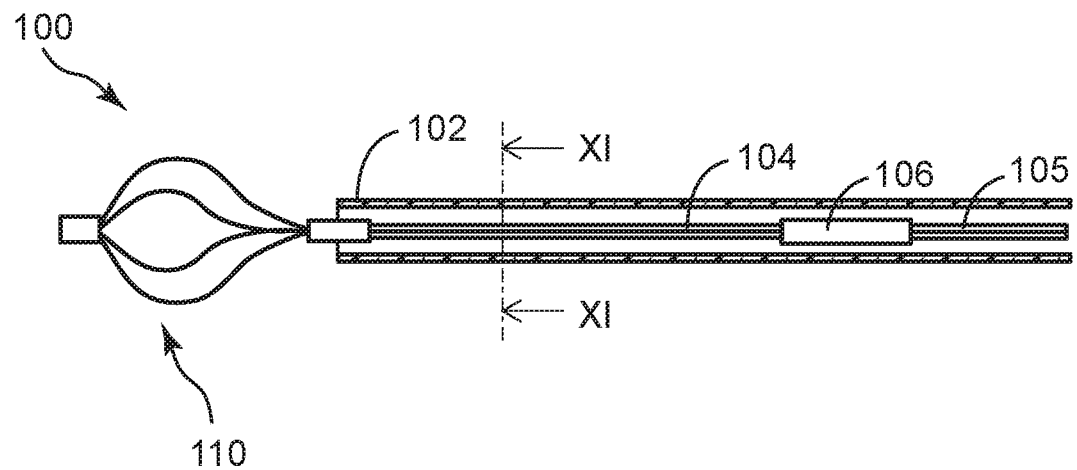
[FIG. 11]
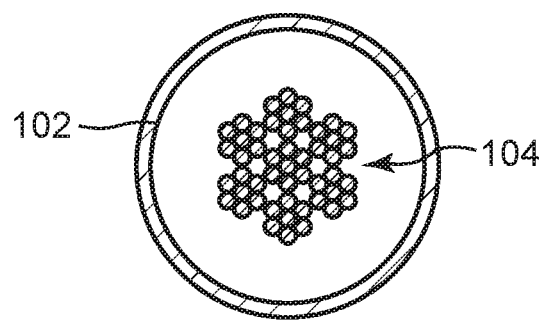

[Fig. 12]
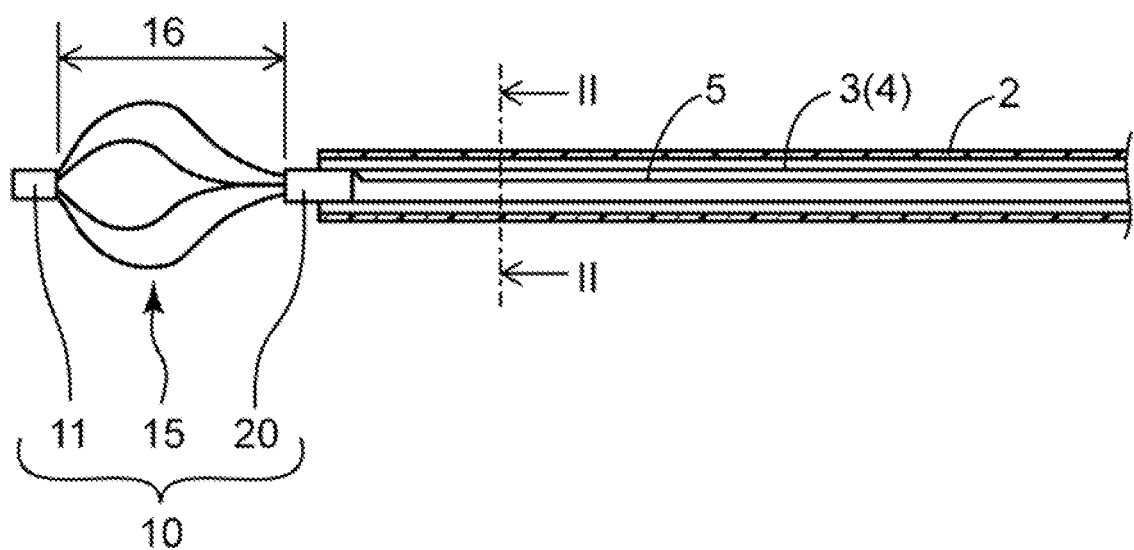
[Fig. 13]
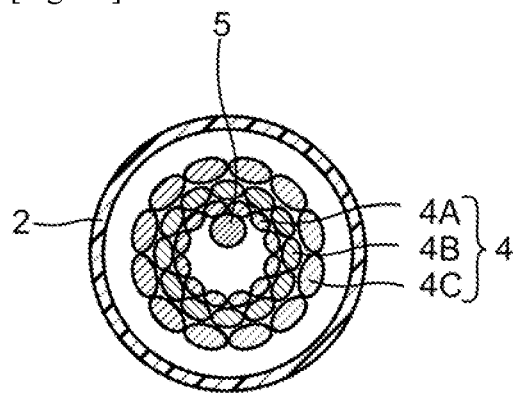

BASKET CATHETER, METHOD FOR PRODUCING THE SAME AND MEDICAL TREATMENT INSTRUMENT

TECHNICAL FIELD

The present invention relates to a catheter that is capable of capturing a foreign matter in its basket and relates to a medical treatment instrument having the same.

BACKGROUND ART

A treatment for a calculus formed in a bile duct or urethra employs basket catheter (forceps) in which SUS twisted wires or shape memory alloy wires, such as Ni—Ti, are woven into a cage shape and employs a balloon catheter for calculus removal. In the basket catheter, a basket part that captures a foreign matter is configured in the following manner. Metal wires are fixed at two points of the catheter: one is at a distal end of the catheter and the other is at a place that is proximal to the distal end. Between those two fixing points, the wires are bent or twisted into a spiral shape to form the cage shape. The basket part is, for example, stored in a resin sheath during delivery into a diseased region and expanded to the cage shape by being exposed from the distal end of the sheath upon capture of a foreign matter. For accurate removal of a foreign matter in a short time, it is necessary to efficiently transmit rotational torque by handle operation at a hand side to the basket part to change a position of the metal wires forming the basket, thereby easily taking in the foreign matter or hooking it.

FIGS. 10 to 11 show a conventional basket catheter. As shown in FIG. 10, the conventional basket catheter 100 has a basket part 110 that can be stored in an outer tubular member 102. The basket part 110 and a handle at a hand side (not illustrated) are connected together through wire members 104 and 105. The wire members 104 and 105 transmit torque and, in FIG. 10, are connected with one another through a connector pipe 106. The wire member is, for example, one in which elastic wires that form the basket part are axially disposed in parallel as shown in FIG. 11. Patent Document 1, for example, discloses a medical basket type holding forceps in which twisted wires are axially and more proximally disposed in parallel than a proximal end part of its cage-shaped part and an operation wire is further connected with the proximal side.

PRIOR ART DOCUMENT

Patent Document

Patent Document 1: JP2005-21195A

SUMMARY OF THE INVENTION

Technical Problem

The holding forceps (basket forceps) disclosed in Patent Document 1 cannot be rotated at a desired angle or in a desired direction in some cases upon its insertion into a body lumen having a meandering shape because the operation wire or the proximal end part (part in which elastic wires are axially disposed in parallel) of the basket part comes into contact with an inner wall of an endoscope or because a lumen of an outer tube is squashed and then the operation wire or the proximal end part is trapped by an acute angle caused by a raising base of a forceps. Especially, in a bending part of a bile duct having a small diameter, the basket wires are disproportionately disposed on the outside of the bending duct. This impedes retention of a sufficiently expanded state of the basket and thus causes trouble upon capture of a calculus in some cases. In addition, this impedes release of a captured calculus into the basket and may impede removal of a catheter itself from the bile duct (impaction). As a result, operative time is prolonged by transition to a treatment for the impaction removal or a surgical operation, and the prolonged operative time might intensify an operative invasion upon a patient. Considering the above, the present invention aims to provide a basket catheter that facilitates capture of a foreign matter by making rotational torque on the proximal side easily transmitted to a basket part and enables observation on the inside of a duct or on a foreign matter, or enables a treatment, such as removal of a captured foreign matter, by inserting a different auxiliary treatment instrument into a lumen of the basket catheter.

Solutions to the Problems

The gist of the present invention is as follows. A basket catheter according to the present invention that can overcome the above problems has a distal side and a proximal side and has an outer tubular member, an inner tubular member disposed in a lumen of the outer tubular member, and an expandable basket part that is disposed on the distal side of the inner tubular member and includes elastic wires. The inner tubular member includes a hollow coil body formed of a wire wound spirally. In the basket catheter according to the present invention, the inner tubular member disposed on the proximal side of the basket part includes the hollow coil body formed of the wire wound spirally, thus facilitating transmission of torque at a hand side to the basket part, and then facilitating capture operation of a foreign matter. In addition, a different auxiliary treatment instrument from the basket catheter can be inserted into a lumen of the inner tubular member, thus enabling observation on the inside of a duct or on a foreign matter, or enabling a treatment, such as removal of a captured foreign matter. This yields effects such as prevention of impaction, an increase in operative options for cases and promotion of a minimally invasive treatment.

Preferably, in the above basket catheter, the hollow coil body includes at least a first layer and a second layer disposed outside the first layer, and a winding direction of the wire in the first layer is opposite to a winding direction of the wire in the second layer.

Preferably, in the above basket catheter, the hollow coil body has the first layer, the second layer disposed outside the first layer, and a third layer disposed outside the second layer, and the winding direction of the wire in the first layer is opposite to the winding direction of the wire in the second layer, and the winding direction of the wire in the second layer is opposite to a winding direction of the wire in the third layer.

Preferably, in the above basket catheter, an added wire extending along a distal and proximal direction is disposed in a lumen of the hollow coil body, and one end part and the other end part of the added wire are fixed to the hollow coil body.

Preferably, in the above basket catheter, the inner tubular member further includes a metal pipe connected with a proximal end part of the hollow coil body.

Preferably, in the above basket catheter, the elastic wires and the inner tubular member are connected together through a tubular connector.

Preferably, the connector includes wire insertion passages; a proximal end part of the elastic wire is inserted from the distal side into each wire insertion passage; and the wire insertion passages are arranged in a circumferential direction.

Preferably, the connector includes on a peripheral wall of the connector a fixing hole communicating with the outside and the wire insertion passage.

Preferably, the connector includes a small-diameter part having a smaller outer diameter on the proximal side than an outer diameter of the small-diameter part on the distal side, and the small-diameter part is inserted into the distal side of the lumen of the inner tubular member.

Preferably, an inner diameter of the connector in the small-diameter part is the same as or larger than an inner diameter of a distal end of the inner tubular member.

The present invention also provides a medical treatment instrument having the above basket catheter, and an auxiliary treatment instrument inserted into the lumen of the inner tubular member. A use of the auxiliary treatment instrument enables observation on the inside of a duct or on a foreign matter, or enables a treatment, such as removal of a captured foreign matter.

Preferably, in the above medical treatment instrument, the auxiliary treatment instrument is a balloon catheter, a microcatheter, a forceps, a laser probe, a fiber scope, an electronic hydraulic lithotripsy probe or a guide wire.

The present invention also provides a method for producing a basket catheter. The gist of the method for producing the basket catheter is as follows. The method includes preparing elastic wires forming an expandable basket part, and a tubular connector connecting an inner tubular member and the elastic wires and including wire insertion passages arranged in a circumferential direction; inserting a proximal end part of the elastic wire into the wire insertion passage from a distal side; and joining the elastic wires and the connector together. In the method for producing the basket catheter according to the present invention, the inner tubular member is adopted as a wire member that transmits rotational torque at the hand side to the basket part, and also the elastic wire and the inner tubular member are connected together through a tubular connector. As a result, the basket catheter into whose lumen an auxiliary treatment instrument can be inserted is achieved.

Preferably, in the above production method, the connector includes on a peripheral wall of the connector a fixing hole communicating with the outside and the wire insertion passage, and a joining agent is injected into the fixing hole when the elastic wires and the connector are joined.

Preferably, in the above production method, the method includes reducing an outer diameter of the proximal end part of the elastic wire before inserting the elastic wire into the wire insertion passage.

Preferably, in the above production method, the method further includes preparing the inner tubular member including a hollow coil body formed of a wire wound spirally; and inserting a proximal end part of the connector into a distal end part of a lumen of the inner tubular member.

Advantageous Effects of the Invention

According to the basket catheter of the present invention, the basket catheter facilitates transmission of rotational torque at the hand side to the basket part and thus facilitates capture operation of a foreign matter. Also, the basket catheter enables a different auxiliary treatment instrument from the basket catheter to be inserted into the lumen of the inner tubular member, thus enabling observation on the inside of a duct or on a foreign matter, or enabling a treatment, such as removal of a captured foreign matter.

According to the medical treatment instrument of the present invention, the auxiliary treatment instrument inserted into the lumen of the inner tubular member enables observation on the inside of a duct or on a foreign matter, or enables a treatment, such as removal of a captured foreign matter.

From the above, according to the basket catheter or the medical treatment instrument, effects such as prevention of impaction, an increase in operative options for cases and promotion of a minimally invasive treatment are achieved.

Also, in the method for producing the basket catheter according to the present invention, the inner tubular member is adopted as the wire member that transmits rotational torque at the hand side to the basket part, and also the elastic wire and the inner tubular member are connected together through the tubular connector. As a result, the basket catheter into whose lumen the auxiliary treatment instrument can be inserted is achieved.

BRIEF DESCRIPTION OF DRAWINGS

FIG. 1 is a plan view (partly a cross-sectional view) showing a distal side of a basket catheter according to an embodiment of the present invention.

FIG. 2 is a cross-sectional view showing the basket catheter in FIG. 1 that is taken along line II-II.

FIG. 3 is a plan view (partly a cross-sectional view) showing a proximal side of the basket catheter according to an embodiment of the present invention.

FIG. 4 is a perspective view showing a connector according to an embodiment of the present invention.

FIG. 5 is a cross-sectional view showing the connector according to an embodiment of the present invention that is taken along an axial direction thereof.

FIG. 6 is a plan view (partly a cross-sectional view) showing a method for producing the basket catheter according to an embodiment of the present invention.

FIG. 7 is a plan view (partly a cross-sectional view) showing the method for producing the basket catheter according to an embodiment of the present invention.

FIG. 8 is a plan view (partly a cross-sectional view) showing the method for producing the basket catheter according to an embodiment of the present invention.

FIG. 9 is a plan view (partly a cross-sectional view) showing the method for producing the basket catheter according to an embodiment of the present invention.

FIG. 10 is a plan view showing a conventional basket catheter.

FIG. 11 is a cross-sectional view showing the basket catheter in FIG. 10 that is taken along line XI-XI.

FIG. 12 is another embodiment as shown in FIG. 1 which further includes an additional wire.

FIG. 13 is another embodiment as shown in FIG. 2 which further includes an additional wire.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

1. Basket Catheter and Medical Treatment Instrument

In the present invention, a basket catheter has a distal side and a proximal side, is a medical treatment instrument having a cage-shaped basket that captures a foreign matter in a body, such as a calculus, and includes a basket forceps. Hereinafter, the basket catheter may be simply referred to as "catheter". First, whole structure of the catheter is described by referring to FIG. 1. FIG. 1 is a plan view (partly a cross-sectional view) showing a distal side of a catheter 1 according to the present invention, and FIG. 2 is a cross-sectional view showing the catheter 1 in FIG. 1 that is taken along line II-II.

In the present invention, a proximal side of the catheter 1 refers to a direction of a hand side of a user (operator) against an extension direction of the catheter 1, and the distal side refers to an opposite direction to the proximal side (that is, a direction of a treatment target side). In addition, a direction from the proximal side to the distal side of the catheter 1 is referred to as an axial direction or a distal and proximal direction.

The catheter 1 has an outer tubular member 2, an inner tubular member 3 that is disposed in a lumen of the outer tubular member 2, and an expandable basket part 10 that is disposed on the distal side of the inner tubular member 3 and includes elastic wires 15.

The outer tubular member 2 prevents the elastic wires 15 of the basket part 10 from damaging a forceps opening and the inside of a forceps channel of an endoscope, body tissues other than a foreign matter or the like while the elastic wires 15 are being sent from the forceps opening of the endoscope to near the foreign matter through the forceps channel.

Examples of the outer tubular member 2 include a resin tube extruded by extrusion molding, a tubular body formed by disposing a single wire or twisted wire of a wire with a certain pattern, a metal pipe or a combination of these. Examples of the tubular body in which the wires are disposed with a certain pattern include a tubular body having network structure formed of the wires simply crossing one another or of the wires that are woven together, and a coil formed of the wire that is wound. Neither a type of the network structure nor turns and density of the coil are limited. The coil may have winds with a certain density in the whole axial direction or may have winds with different density depending upon a position in the axial direction. To enhance flexibility of the metal pipe, a groove may be formed in a spiral shape on an outer surface of the metal pipe. Preferably, the groove is formed on the outer surface of a place that is distal to a center of the metal pipe in the axial direction. The groove does not have to be formed on the outer surface of a place that is proximal to the center of the metal pipe in the axial direction.

The outer tubular member 2 is preferably made of resin or a metal. Examples of the resin forming the outer tubular member 2 include polyamide resin, polyester resin, polyurethane resin, polyolefin resin, fluorine resin, vinyl chloride resin, silicone resin and natural rubber. The above resin may be used alone or in combination of two or more sorts. Preference is given to polyamide resin, polyester resin, polyurethane resin, polyolefin resin and fluorine resin. Examples of the metal forming the outer tubular member 2 include stainless steel, such as SUS304 and SUS316, platinum, nickel, cobalt, chromium, titanium, tungsten, gold, Ni—Ti alloy, Co—Cr alloy or combination of these. The wire made of Ni—Ti alloy is especially excellent in a shape memory property and high elasticity. The wire may also be a fiber material, such as polyarylate fiber, aramid fiber, ultrahigh molecular weight polyethylene fiber, PBO fiber and carbon fiber. The fiber material may be a monofilament or multifilament. Also, the tubular body made of the resin and provided with a stiffener, such as the metal wire, may be used as the outer tubular member 2.

The outer tubular member 2 may be configured from a single layer or multiple layers. In addition, one part of the outer tubular member 2 may be configured from a single layer, and the other parts thereof may be configured from multiple layers, in the axial direction.

An inner tubular member 3 is disposed in a lumen of the outer tubular member 2. The inner tubular member 3 includes a hollow coil body 4 formed of a wire wound spirally. The inner tubular member 3 of the basket catheter 1 according to the present invention that includes the hollow coil body 4 in this manner easily transmits torque at a hand side to the basket part 10 and thus facilitates capture operation of a foreign matter. In addition, a different auxiliary treatment instrument from the basket catheter 1 can be inserted into a lumen of the inner tubular member 3 so that this insertion enables observation on the inside of a duct or a foreign matter, or enables a treatment, such as removal of a captured foreign matter. This yields effects such as prevention of impaction, an increase in operative options for cases and promotion of a minimally invasive treatment.

The inner tubular member 3 may include the hollow coil body 4 partly in the distal and proximal direction of the catheter 1 or may include the hollow coil body 4 wholly in the axial direction of the inner tubular member 3. In a case where the inner tubular member 3 partly includes the hollow coil body 4, the other parts than the hollow coil body 4 may be configured in the same manner as the outer tubular member 2. The inner tubular member 3, though not illustrated, preferably further includes the metal pipe connected with a proximal end part of the hollow coil body 4. Provision of the hollow coil body 4 further facilitates transmission of torque at a hand side to the basket part 10, and provision of the metal pipe can reduce an extension ratio of the inner tubular member 3 in the axial direction.

The hollow coil body 4 is formed of one or more of the wires wound spirally. Density (winding interval) of the hollow coil body 4 is not limited, and a tight winding, pitch winding or combination of these may be adopted. In the hollow coil body 4, one wire is preferably in contact with another adjacent wire at least partly in the distal and proximal direction of the basket catheter 1. More preferably, the adjacent wires are in contact with one another wholly in the distal and proximal direction. The contact of the adjacent wires achieves the hollow coil body 4 that is excellent in torque transmission and responsiveness.

In a case where the wire configuring the hollow coil body 4 is a single wire body formed of a single wire, a cross-sectional shape of the wire in the axial direction may be a circular shape, oval shape, polygonal shape or combination of these.

In a case where the wire is a multiple wire body formed of single wires wound spirally, even the following number of the wire is acceptable: two or more, three or more and four or more, or 20 or less, 15 or less, 12 or less, 10 or less and eight or less.

The hollow coil body 4 is preferably formed, as a hollow body having no core, by twisting the wires. In the hollow coil body 4, a twisting direction of the wire may be a Z-twist or S-twist, but is not particularly limited thereto.

The wire forming the hollow coil body 4 is preferably made of resin or a metal. A material forming the wire may be the resin or the metal that forms the outer tubular member 2. The wire is preferably made of platinum and tungsten to stabilize a shape of the hollow coil body 4.

The hollow coil body 4 may be a single-layer coil or a multi-layer coil having layers. In a case where the hollow coil body 4 includes the layers, at least either the winding direction or a winding interval of the wires preferably differs on each layer. In a case where the hollow coil body 4 is a multi-layer coil, an outer diameter of the wire of each layer may be the same or different. In the hollow coil body 4, for example, an outer diameter of the wire of an outer layer may be larger or smaller than an outer diameter of the wire of an inner layer.

The hollow coil body 4 includes at least a first layer 4A and a second layer 4B disposed outside the first layer 4A. A winding direction of the wire in the first layer 4A is preferably opposite to a winding direction of the wire in the second layer 4B. Contact of the first layer 4A and the second layer 4B, which respectively have the opposite winding directions to one another, can prevent extension of the hollow coil body 4 in the axial direction.

The hollow coil body 4 has the first layer 4A, the second layer 4B disposed outside the first layer 4A, and a third layer 4C disposed outside the second layer 4B. The winding direction of the wire in the first layer 4A is preferably opposite to the winding direction of the wire in the second layer 4B, and the winding direction of the wire in the second layer 4B is preferably opposite to a winding direction of the wire in the third layer 4C. Hence, the winding directions of the wires of the first layer 4A and the third layer 4C are preferably the same. Contact of the first layer 4A and the second layer 4B, and the second layer 4B and the third layer 4C, each of which has the respectively opposite winding directions, can even further prevent extension of the hollow coil body 4 in the axial direction. In a case where the hollow coil body 4 is formed, as a three-layer hollow body having no core, by twisting the wires, the first layer 4A, second layer 4B and third layer 4C may have a S-twist, Z-twist and S-twist respectively or may have a Z-twist, S-twist and Z-twist respectively.

In a lumen of the hollow coil body 4 is disposed an additional wire 5 (hereinafter may be referred to as "stiffening wire") extending along the distal and proximal direction. One end part and the other end part of the additional wire 5 are preferably fixed to the hollow coil body 4. This disposition of the stiffening wire in the lumen of the hollow coil body 4 can also prevent extension of the hollow coil body 4 in the axial direction.

In the lumen of the outer tubular member 2 but outside of the hollow coil body 4 is disposed the additional wire 5 (stiffening wire) extending along the distal and proximal direction. One end part and the other end part of the additional wire 5 are preferably fixed to the hollow coil body 4. This disposition of the stiffening wire outside the hollow coil body 4 can also prevent extension of the hollow coil body 4 in the axial direction.

The stiffening wire is preferably made of resin or a metal that is hard to extend in the axial direction and has biocompatibility. An example of a material forming the stiffening wire includes the material forming the wire forming the hollow coil body 4. The material may be, for example, platinum, tungsten, titanium, gold or alloy of these, or stainless steel or polyolefin resin, such as polypropylene resin. Especially, the wire made of polypropylene resin is preferably used as the stiffening wire from a perspective of enhancements of flexibility and delivery performance of the catheter 1 and production cost saving.

A shape of the stiffening wire may be, for example, a linear shape, a wave shape, a spiral shape or a combination shape of these, but is not particularly limited thereto.

The stiffening wire may be directly fixed or indirectly fixed through a different member to the hollow coil body 4. The stiffening wire may be fixed on an inner or outer surface of the hollow coil body 4 or may be fixed on a proximal end surface or a distal end surface thereof.

Inner surfaces of the outer tubular member 2 and the inner tubular member 3 may be coated with a coating agent to protect the outer tubular member 2 and the inner tubular member 3 from a fluid, such as a contrast agent and chemical. In addition, the inner surface of the inner tubular member 3 may be coated with lubricant to enhance slipperiness of a guide wire to the inner tubular member 3. Further, the inner surface of the outer tubular member 2 may be coated with lubricant to enhance slipperiness of the inner tubular member 3 to the outer tubular member 2. As the coating agent and lubricant, commonly known ones may be used.

FIG. 3 shows example structure of the proximal side of the catheter 1 shown in FIG. 1. As shown in FIG. 3, a proximal end side of the inner tubular member 3 may be connected with a holding member 50 to enhance operability of the inner tubular member 3. An example of the holding member 50 includes a tubular member into which the proximal end side of the inner tubular member 3 can be inserted.

A proximal end side of the outer tubular member 2 may be connected with an auxiliary holding member 51 for holding the outer tubular member 2 for the purpose of facilitating an adjustment of relative positions of the outer tubular member 2 and the inner tubular member 3. An example of the auxiliary holding member 51 includes a tubular member into whose lumen the proximal end side of the outer tubular member 2 can be inserted. Materials for the holding member 50 and the auxiliary holding member 51 may be, for example, synthetic resin, such as ABS and polycarbonate, or foamed plastic, such as polyurethane foam. A lumen of the holding member 50 may be communicated with the lumen of the inner tubular member 3. The lumen of the holding member 50 may function, other than an insertion passage for the guide wire, as a passage for a medicament or for a fluid or the like in a body lumen. In addition, a lumen of the auxiliary holding member 51 that communicates, in the lumen of the outer tubular member 2, with the outside of the inner tubular member 3 may function as a passage for a medicament or for a fluid or the like in a body lumen.

The inner tubular member 3 and the holding member 50, and the outer tubular member 2 and the auxiliary holding member 51 may be joined by a conventionally known joining means or method, such as an adhesive and heat welding. The holding member 50 is disposed more proximally than the auxiliary holding member 51. A proximal end of the auxiliary holding member 51 may be provided with, for example, a ring-shaped resistance member 52. This provision can prevent an unintentional shift of a position of the auxiliary holding member 51 relative to the holding member 50 so that the relative positions of the outer tubular member 2 and the inner tubular member 3 can be fixed.

The basket catheter 1 has the expandable basket part 10 that is disposed on the distal side of the inner tubular member 3 and includes the elastic wires 15. The basket part 10 is provided for capture of a foreign matter in a body. In the basket part 10, the elastic wires 15 are preferably fixed, as shown in FIG. 1, at two points: one is the distal side and the other is the proximal side. This disposition forms a capture part 16 that captures, between the two fixed parts, a foreign matter. By protruding the elastic wires 15 from the outer tubular member 2, the elastic wires 15 expand outward in a radial direction of the outer tubular member 2, thus enabling capture of a foreign matter into the capture part 16.

The elastic wire 15 is a linear member having elasticity and is preferably made of shape memory alloy or shape memory resin. The elastic wire 15 may be, for example, a metal wire of a single wire or a twisted wire that is made of stainless steel, such as SUS304 and SUS316, platinum, nickel, cobalt, chromium, titanium, tungsten, aluminum, gold, silver, Ni—Ti alloy, Co—Cr alloy or the like. Preference is given to the metal wire made of Ni—Ti alloy. The number of the elastic wire 15 is not limited, but, for example, even the following number is acceptable: three or more, four or more and five or more, and ten or more, or 20 or less and 15 or less.

In the capture part 16, the elastic wire 15 preferably has a part that bends (bending part). At the bending part, the elastic wire 15 may curve or be folded. Also, in the capture part 16, the elastic wire 15 may be spirally formed. The capture part 16 formed in this manner facilitates capture of a foreign matter.

In the basket part 10, the elastic wires 15 are preferably fixed with one another on the distal end parts. The distal end parts of the elastic wires 15 may be fixed by an end tip member 11. In addition, the elastic wires 15, though not illustrated, may be fixed with one another by heat welding, silver brazing or adhesion.

The end tip member 11 preferably has a wire insertion hole 12 into which the distal end parts of the elastic wires 15 are inserted from the proximal side (refer to FIG. 6). The end tip member 11, though not illustrated, may have the wire insertion holes 12 into which the distal end parts of the elastic wires 15 are inserted from the proximal side.

Examples of a material forming the end tip member 11 include the resin, the metal or the combination of these that preferably forms the outer tubular member 2. However, the metal forming the end tip member 11 is preferably stainless steel or Ni—Ti alloy.

The end tip member 11, though not illustrated, may be provided with an insertion passage for a treatment instrument into which an auxiliary treatment instrument, which is different treatment instrument from the basket catheter 1, is inserted. The insertion passage for a treatment instrument preferably extends along the axial direction of the inner tubular member 3. In addition, a central axis of the passage for a treatment instrument of the end tip member 11 is preferably aligned with a central axis of the inner tubular member 3. Providing the end tip member 11 with the passage for a treatment instrument in this manner facilitates a more distal disposition of a distal end of an auxiliary treatment instrument than the distal end of the catheter 1. This disposition enables a chemical or a contrast agent to be poured over the distal side of a foreign matter with the auxiliary treatment instrument even after the foreign matter is captured with the capture part 16. The insertion passage for a treatment instrument preferably extends along the axial direction of the inner tubular member 3 to facilitate insertion of the auxiliary treatment instrument.

In a radial direction of the inner tubular member 3, an outer diameter of the end tip member 11 is preferably larger than an inner diameter of the outer tubular member 2. This difference in diameters lets the end tip member 11 stopped by the distal end of the outer tubular member 2, even though the capture part 16 is stored into the outer tubular member 2. Consequently, this stoppage can prevent the basket part 10 from moving excessively to the proximal side of the outer tubular member 2. Also, upon performing an operation after storing the capture part 16, the capture part 16 can immediately be protruded from the outer tubular member 2, thus enabling to perform the operation efficiently.

As shown in FIG. 1, the elastic wires 15 are preferably fixed on the proximal side. Specifically, the elastic wires 15 and the inner tubular member 3 are preferably connected together through a tubular connector 20. FIGS. 4 and 5 show an embodiment of the tubular connector 20. The connector 20 is formed into a tubular shape so that the connector 20 and the lumen of the inner tubular member 3 can communicate with one another. This communication enables an auxiliary treatment instrument inserted into the lumen of the inner tubular member 3 to reach the capture part 16 or a place that is distal to the capture part 16 through a lumen 24 of the connector 20. This reachability enables observation on the inside of a duct or on a foreign matter, and a treatment, such as removal of a foreign matter, thus yielding effects, such as prevention of impaction, an increase in operative options for cases and promotion of a minimally invasive treatment.

A material forming the connector 20 preferably has biocompatibility and may be the one that is exemplified as the preferable material forming the end tip member 11.

A shape of the connector 20 may be a tubular shape or a polygonal tubular shape, but the shape of the connector 20 is preferably a tubular shape to enhance slipperiness to the outer tubular member 2.

The connector 20 is stored, with the capture part 16, into the outer tubular member 2. Hence, an outer diameter of the connector 20 is smaller than the inner diameter of the outer tubular member 2.

As shown in FIG. 4, the connector 20 includes a wire insertion passages 21 (for example, 21*a*, 21*b*, 21*c* and 21*d*). Proximal end parts of the elastic wires 15 are inserted from the distal side into each wire insertion passage, and the wire insertion passages 21 are preferably arranged in a circumferential direction. In this case, the wire insertion passages 21 are preferably provided on a peripheral wall of the connector 20. The elastic wires 15 circumferentially arranged in this manner on the outside of the lumen 24 of the connector 20 in the radial direction, the outside in this case means a periphery of the lumen 24, can prevent an auxiliary treatment instrument from being obstructed by the elastic wires 15 upon an advance and retreat of the auxiliary treatment instrument in the axial direction.

An inlet of the wire insertion passage 21 is preferably provided on an end surface of the distal side of the connector 20, thereby facilitating insertion of the elastic wire 15 from the distal side.

Into one wire insertion passage 21 may be inserted one or more of the elastic wires 15. However, one elastic wire 15 is preferably inserted into one wire insertion passage 21 to firmly fix the elastic wire 15 and the connector 20 together. For this reason, an inner diameter of the wire insertion passage 21 is preferably larger than an outer diameter of the elastic wire 15. The inner diameter of the wire insertion passage 21 is preferably 1.5 or less times, more preferably 1.2 or less times and further preferably 1.1 or less times as large as the outer diameter of the elastic wire 15.

The number of the provided wire insertion passage 21 may correspond to the number of the elastic wire 15. The number may be, for example, three or more, four or more, five or more, or six or more but, for example, 12 or less, or 10 or less from a perspective of facilitating production of the connector 20.

An extension direction of the wire insertion passage 21 is not limited, but at least a part of the wire insertion passage 21 preferably extends along the axial direction of the inner tubular member 3, and more preferably, the whole wire insertion passage 21 extends along the axial direction of the inner tubular member 3. This extension direction facilitates insertion of the proximal end part of the elastic wire 15 into the wire insertion passage 21 and simultaneously can prevent buckling of the elastic wire 15.

The wire insertion passage 21 may be provided in a manner that it penetrates the connector 20 in the axial direction. Specifically, the inlet of the wire insertion passage 21 may be provided on the end surface of the distal side of the connector 20, and its outlet may be provided on an end surface of the proximal side of the connector 20. The wire insertion passage 21 provided in this manner can lengthen the insertion passage. In addition, the wire insertion passage 21 may have the same length as an entire length of the connector 20 in the axial direction of the inner tubular member 3. Such a wire insertion passage 21 can be easily formed, thus enhancing productivity of the connector 20.

On the other hand, a disposition of a proximal end of the wire insertion passage 21 may be distal to a proximal end of the connector 20. That is, the wire insertion passage 21 may have shorter length than the entire length of the connector 20. Upon insertion of the elastic wire 15 into the wire insertion passage 21, the elastic wire 15 comes into contact with an end of the wire insertion passage 21, thus enabling a constant length of a part of the elastic wire 15 that corresponds to the capture part 16. In the distal and proximal direction, a length of the wire insertion passage 21 may be shorter than the entire length of the connector 20 as long as the connector 20 and the elastic wire 15 can be joined together. The length of the wire insertion passage 21 may be 75% or less or 50% or less of the entire length of the connector 20, or may be acceptably 5% or more, 10% or more, or 20% or more of the entire length of the connector 20.

The wire insertion passages 21 are preferably disposed on the connector 20 in the circumferential direction at regular intervals. Also, the wire insertion passages 21 may be disposed rotationally symmetrically, with a central axis of the connector 20 being a center thereof. This disposition of the wire insertion passage 21 enables formation of a shape of the capture part 16 that easily captures a foreign matter.

The connector 20 preferably has a longer length in the axial direction than length of its maximum outer diameter. This facilitates enough allocation of the length of the wire insertion passage 21.

As shown in FIGS. 4 and 5, the connector 20 preferably includes on the peripheral wall of the connector 20 a fixing hole 22 communicating with the outside and the wire insertion passage 21. Injection of a joining agent 30 from the fixing hole 22 can fix the elastic wire 15 and the connector 20 together more firmly.

One or more of the fixing holes 22 may be provided on one insertion passage, but the fixing hole 22 is preferably provided one-to-one on the insertion passage to prevent strength deterioration of the connector 20. An axial direction of the fixing hole 22 preferably crosses the axial direction of the wire insertion passage 21 and more preferably crosses orthogonally.

An inner diameter of the fixing hole 22 may be larger or smaller than the diameter of the wire insertion passage 21. Also, the fixing hole 22 in the axial direction may have shorter length than the wire insertion passage 21 in the axial direction.

The fixing hole 22 is preferably provided on a place that is distal to the proximal end of the wire insertion passage 21. The fixing hole 22 is preferably provided on a section of 25% or more and 75% or less and more preferably 40% or more and 60% or less, when the proximal end and a distal end of the wire insertion passage 21 represent 0% and 100% respectively in the axial direction. This provision makes the joining agent 30 that is injected from the fixing hole 22 easily spread in the wire insertion passage 21, thus enabling to firmly fix the elastic wire 15 and the connector 20 together.

The joining agent 30 that is inserted into the fixing hole 22 may be, for example, solder, such as silver solder, or an adhesive, such as an acrylic adhesive, an epoxy adhesive and a urethane adhesive.

A joining method of the connector 20 and the inner tubular member 3 is not limited. However, as shown in FIGS. 4 and 5, the connector 20 includes a small-diameter part 23 having a smaller outer diameter on the proximal side than an outer diameter of the small-diameter part 23 on the distal side, and the small-diameter part 23 is preferably inserted into the distal side of the lumen of the inner tubular member 3. Providing the connector 20 with such a small-diameter part 23 enables easy connection of the inner tubular member 3 and the connector 20 together.

The small-diameter part 23 preferably has in the axial direction a length that is half or less the entire length of the connector 20. Setting the length of the small-diameter part 23 in this manner enables firm connection with the inner tubular member 3.

In the above small-diameter part 23 and a non-small-diameter part that is distal to the small-diameter part 23, the connector 20 preferably has a constant inner diameter. Setting the diameter in this manner yields preferable slipperiness of an auxiliary treatment instrument inserted into the lumen 24 of the connector 20.

An outer diameter of the small-diameter part 23 is, compared to an outer diameter of the non-small-diameter part, preferably 95% or less, more preferably 90% or less, and further preferably 80% or less, and also preferably 60% or more and more preferably 65% more. This facilitates connection with the inner tubular member 3 while allocating an enough space in an insertion passage for an auxiliary treatment instrument.

The inner diameter of the connector 20 in the small-diameter part 23 is preferably the same as or larger than an inner diameter of the inner tubular member 3 on its distal end. This renders an auxiliary treatment instrument less likely to hit against a joint between members of the inner tubular member 3 and the connector 20 upon insertion of the auxiliary treatment instrument into the lumen from the proximal side of the inner tubular member 3, thus enabling smooth movement of the auxiliary treatment instrument from the distal side to the proximal side. In addition, once a part of the auxiliary treatment instrument in the axial direction passes the joint between the inner tubular member 3 and the connector 20, operation of pulling the auxiliary treatment instrument out of the inner tubular member 3 can be performed smoothly. Also, the inner diameter of the connector 20 in the small-diameter part 23 may be smaller than the inner diameter of the inner tubular member 3 on its distal end. In addition, the inner diameter of the connector 20 in the small-diameter part 23 on its distal end is preferably the same as the inner diameter of the inner tubular member 3 on its distal end. The connector 20 and the inner tubular member 3 have no step between themselves, and thus the auxiliary treatment instrument can be inserted further smoothly.

The outer diameter of the connector 20 in the small-diameter part 23 is preferably the same as or smaller than the inner diameter of the inner tubular member 3 on its distal end. Setting the inner diameters of the connector 20 and the inner tubular member 3 in this manner enables the proximal side of the connector 20 to be inserted into a distal end side of the inner tubular member 3.

Upon providing the connector 20 with the small-diameter part 23, the wire insertion passage 21 and the fixing hole 22 are preferably provided on the non-small-diameter part that is distal to the small-diameter part 23. Forming the wire insertion passage 21 and the fixing hole 22 in this manner can prevent strength deterioration of the connector 20.

In addition, the present invention includes a medical treatment instrument having the above-described basket catheter 1 and an auxiliary treatment instrument inserted into the lumen of the inner tubular member 3. According to the medical treatment instrument of the present invention, the auxiliary treatment instrument inserted into a lumen of the basket catheter 1 enables observation on the inside of a duct or on a foreign matter, or enables a treatment, such as removal of a captured foreign matter. This yields effects such as prevention of impaction, an increase in operative options for cases and promotion of a minimally invasive treatment.

Examples of the auxiliary treatment instrument include a balloon catheter, a micro-catheter, a forceps, a laser probe, a fiber scope, an electronic hydraulic lithotripsy probe (Electronic hydraulic lithotripsy: EHL) or a guide wire. Using the balloon catheter, the forceps, the laser probe and the EHL enables removal of a foreign matter caught in the basket part 10, thus enabling to prevent the occurrence of the impaction. The micro-catheter can be used for injection of a contrast agent into a place that is distal to the distal end of the basket catheter 1 or used for wire backup to deliver the basket catheter into a region into which the guide wire is difficult to be inserted. Also, the fiber scope can be used for observation on a state of a region that is distal to the distal end of the basket catheter 1. The guide wire can be a guide for a delivery route or a delivery location of the basket catheter 1.

2. Method for Operating the Medical Treatment Instrument

A method for operating the medical treatment instrument according to the present invention preferably includes disposing the auxiliary treatment instrument in the lumen of the inner tubular member 3. Specifically, a distal end part of the auxiliary treatment instrument is preferably inserted from the proximal side of the inner tubular member 3. This corresponds to a preparation for protruding the auxiliary treatment instrument from a distal end of the inner tubular member 3.

The above operation method includes protruding the auxiliary treatment instrument outside from the distal end of the inner tubular member 3. Specifically, a proximal end of a treatment part provided on the distal side of the auxiliary treatment instrument is preferably disposed more distally than the distal end of the inner tubular member 3. This disposition enables, by the auxiliary treatment instrument, observation on the inside of a duct or on a foreign matter, or enables a treatment, such as removal of a captured foreign matter, in addition to capture of a target, such as the foreign matter, by the basket catheter 1. Before protruding the auxiliary treatment instrument outside from the distal end of the inner tubular member 3, capturing a target with the basket part 10 may be performed.

The above operation method preferably further includes retaining a target with the basket part 10 and removing the target retained by the basket part 10 with the auxiliary treatment instrument (removal step). Even though the target, such as a calculus, retained by the basket part 10 cannot be released, the target can be removed with the auxiliary treatment instrument, and thus, the occurrence of impaction can be prevented. To remove the target, the auxiliary treatment instrument is preferably a balloon catheter, a forceps, a laser probe or an EHL. In a case where the auxiliary treatment instrument is the balloon catheter, for example, the target can be removed in the following manner. A balloon is inflated to apply a load to the target from the inside and widen intervals of the elastic wires 15. Consequently, the target trapped by the elastic wires 15 is pushed out of the basket part 10. In the above removal step, the target may be broken by using the forceps, laser probe or EHL of the auxiliary treatment instrument. Also, in the above removal step, the target is preferably held and released from the basket part 10 by the forceps of the auxiliary treatment instrument.

The above operation method preferably further includes disposing the above auxiliary treatment instrument more distally than to the distal end of the above basket catheter 1. In this case, the auxiliary treatment instrument is preferably the micro-catheter, fiber scope or the guide wire. Such an auxiliary treatment instrument can be preferably used to check a target located in a place that is distal to the distal end of the basket catheter 1 or check a state of a treatment target region, or used to deliver the basket catheter 1 into a region into which the guide wire is difficult to be inserted.

In a case where the auxiliary treatment instrument is the micro-catheter, the contrast agent may be poured from a distal end of the micro-catheter. This enables the contrast agent to be injected over a target that is distal to the distal end of the basket catheter 1, thus enabling observation on the target that is distal to the distal end of the basket catheter 1 or on the state of the treatment target region.

3. Method for Producing Basket Catheter

The basket catheter 1 described in "1. Basket Catheter and Medical Treatment Instrument" can be produced by the following method. A method for producing the basket catheter 1 according to the present invention includes: preparing elastic wires 15 forming an expandable basket part 10, and a tubular connector 20 connecting an inner tubular member 3 and the elastic wires 15 and including wire insertion passages 21 arranged in a circumferential direction; inserting a proximal end part of the elastic wire 15 into the wire insertion passage 21 from a distal side; and joining the elastic wires 15 and the connector 20 together.

First, the elastic wires 15 and the tubular connector 20 including the wire insertion passages 21 are prepared.

The elastic wire 15 form the expandable basket part 10. The elastic wire 15 preferably employs a metal material or resin that is prepared in a manner that the wire is heated in a state of being bent into a desired shape and then shape-memorized. Heating temperature and heating time may be appropriately set, depending upon a material of the wire. Subjecting to this step, the wire is processed into a form that is suitable to capture a target. As another method, a wire that has been bent into a desired shape in advance may be prepared.

The tubular connector 20 connects the inner tubular member 3 and the elastic wires 15 together and includes the wire insertion passages 21 arranged in the circumferential direction. Into one wire insertion passage 21 may be inserted one or more of the elastic wires 15, but insertion of one elastic wire 15 is preferred.

The connector 20 preferably includes on a peripheral wall of the connector 20 a fixing hole 22 communicating with the outside and the wire insertion passage 21. This can firmly fix the connector 20 and the elastic wire 15 together. The wire insertion passage 21 and the fixing hole 22 may have the structure described in "1. Basket Catheter and Medical Treatment Instrument". The wire insertion passage 21 and the fixing hole 22 may be formed by drilling, etching or laser processing.

The present invention may further include preparing the end tip member 11. The end tip member 11 can fix the elastic wires 15 on their distal end parts.

In addition, the present invention preferably further includes preparing the inner tubular member 3 including a hollow coil body 4 formed of a wire wound spirally. This facilitates transmission of torque at a hand side to the basket part 10, thus facilitating capture operation of a foreign matter.

The present invention also includes a method for producing the basket catheter 1 that includes fixing the distal end parts of the elastic wires 15. A method for fixing the distal end parts of the elastic wires 15 is, for example, a joining method, in a case of including preparing the end tip member 11, in which, as shown in FIG. 6, the distal end parts of the elastic wires 15 (for example, 15a, 15b, 15c and 15d) are inserted into the wire insertion hole 12 provided on the end tip member 11 and then the end tip member 11 into which the elastic wires 15 are inserted is swaged (crimped). Examples of a method for fixing the distal end parts of the elastic wires 15 further include joining methods by melting and joining with laser or the like, welding, brazing, and adhesion with an adhesive, such as an acrylic adhesive, an epoxy adhesive, a urethane adhesive or the like. Without being limited to such a method, the distal end parts of the elastic wires 15 may be fixed together by heat welding.

Next, as shown in FIG. 7, the proximal end part of the elastic wire 15 is inserted into the wire insertion passage 21 from the distal side. For this reason, the inner diameter of the wire insertion passage 21 is preferably the same as or larger than an outer diameter of the proximal end part of the elastic wire 15.

The above production method may, though not illustrated, include reducing the outer diameter of the proximal end part of the elastic wire 15, before inserting the elastic wire 15 into the wire insertion passage 21. Reducing the outer diameter of the proximal end part of the elastic wire 15 in this manner facilitates insertion into the wire insertion passage 21. Examples of a method for reducing the outer diameter of the proximal end part of the elastic wire 15 include a method of cutting the proximal end part of the elastic wire 15 with a blade and a method of crushing the proximal end part by pressing it. An outer diameter of the insertion part inserted into the wire insertion passage 21 is preferably 95% or less, more preferably 90% or less and further preferably 70% or less of an outer diameter of the non-insertion part, which is not inserted, and may be acceptably 40% or more, or 50% or more of the outer diameter of the non-insertion part.

The above production method includes joining the elastic wires 15 and the connector 20 together. Examples of a joining method of the elastic wire 15 and the connector 20 include swaging (crimping) of the connector 20 into which the elastic wire 15 is inserted, melting and joining with laser or the like, welding, brazing, and adhesion with an adhesive. To prevent an occurrence of uneven joining strength, the elastic wire 15 and the connector 20 are preferably adhered together with brazing or the adhesive.

As shown in FIG. 8, the connector 20 includes on the peripheral wall of the connector 20 the fixing hole 22 communicating with the outside and the wire insertion passage 21 (21b and 21d are not illustrated). When the elastic wires 15 and the connector 20 are joined, the joining agent 30 is preferably injected into the fixing hole 22. The fixing hole 22 provided on the connector 20 may have the structure described above. Examples of the joining agent 30 include solder, such as silver solder, and an adhesive, such as an acrylic adhesive, an epoxy adhesive and a urethane adhesive.

The above production method may include joining the connector 20 and the inner tubular member 3 together. The above production method, as shown in FIG. 9, preferably includes inserting a proximal end part of the connector 20 into a distal end part of a lumen of the inner tubular member 3. Inserting the connector 20 into the inner tubular member 3 in this manner facilitates junction of the inner tubular member 3 and the connector 20. As shown in FIG. 9, into the lumen of the inner tubular member 3 may be inserted the small-diameter part 23 with which the connector 20 is preferably provided. Also, as another embodiment, a distal end part of the inner tubular member 3 may be inserted into a proximal end part of the lumen 24 of the connector 20. As yet another embodiment, the proximal end part of the connector 20 and the distal end part of the inner tubular member 3 may be joined by a method by melting and joining, welding, brazing, adhesion with an adhesive, or the like.

The above production method may include connecting a different tubular member (hereinafter called "pipe") with a proximal end part of the inner tubular member 3. Because the pipe is a member provided to facilitate operation of the holding member 50, the pipe preferably has higher hardness than hardness of the inner tubular member 3. The pipe is preferably made of a metal material, such as stainless steel. Examples of a joining method of the pipe and the inner tubular member 3 include a method by melting and joining with laser or the like, welding, brazing, and adhesion with an adhesive, or the like in addition to a method of inserting a distal end part of the pipe into a proximal end part of the lumen of the inner tubular member 3.

In addition, the above production method may include connecting the holding member 50 with the proximal end part of the inner tubular member 3, connecting the auxiliary holding member 51 with a proximal end part of the outer tubular member 2 and disposing the inner tubular member 3 in the lumen of the outer tubular member 2.

This application claims the benefit of the priority date of Japanese patent application No. 2017-161611 filed on Aug. 24, 2017. All of the contents of the Japanese patent application No. 2017-161611 filed on Aug. 24, 2017, are incorporated by reference herein.

REFERENCE SIGNS LIST

1: a basket catheter
2: an outer tubular member

3: an inner tubular member
4: a hollow coil body
4A: a first layer, 4B: a second layer, 4C: a third layer
5: an additional wire
10: a basket part
11: an end tip member
12: a wire insertion hole
15, 15a, 15b, 15c, 15d: an elastic wire
16: a capture part
20: a connector
21, 21a, 21b, 21c, 21d: a wire insertion passage
22: a fixing hole
23: a small-diameter part
24: a lumen of the connector
30: a joining agent
50: a holding member
51: an auxiliary holding member
52: a resistance member

The invention claimed is:

1. A basket catheter, comprising:
an outer tubular member;
an inner tubular member disposed in a lumen of the outer tubular member and having a distal end and a proximal end;
an expandable basket part disposed on a distal side of the inner tubular member and including elastic wires, and
a tubular connector having a proximal end and a distal end,
wherein the inner tubular member includes a hollow coil body formed of a wire wound spirally;
the elastic wires and the inner tubular member are connected together through the tubular connector;
the tubular connector has a small-diameter portion at the proximal end, the small-diameter portion has an outer diameter, which is smaller than an outer diameter of the distal end of the tubular connector, and the small-diameter portion is directly connected to the distal end of the inner tubular member so that an inner diameter of the small-diameter portion is the same as or larger than an inner diameter of the distal end of the inner tubular member.

2. The basket catheter according to claim 1,
wherein the hollow coil body includes at least a first layer and a second layer disposed outside the first layer, and
a winding direction of a wire in the first layer is opposite to a winding direction of a wire in the second layer.

3. The basket catheter according to claim 1,
wherein the hollow coil body has a first layer, a second layer disposed outside the first layer, and a third layer disposed outside the second layer,
a winding direction of a wire in the first layer is opposite to a winding direction of a wire in the second layer, and
the winding direction of the wire in the second layer is opposite to a winding direction of a wire in the third layer.

4. The basket catheter according to claim 1, further comprises an additional wire,
wherein the additional wire extends along a distal and proximal direction and is disposed in a lumen of the hollow coil body, and
one end part and the other end part of the additional wire are fixed to the hollow coil body.

5. The basket catheter according to claim 1,
wherein the inner tubular member further includes a metal pipe connected with a proximal end part of the hollow coil body.

6. The basket catheter according to claim 1,
wherein the tubular connector has wire insertion passages,
a proximal end part of each of the elastic wires is inserted from the distal side into each of the wire insertion passages of the tubular connector,
the wire insertion passages are arranged in a circumferential direction.

7. The basket catheter according to claim 6,
wherein the tubular connector includes on a peripheral wall of the tubular connector a fixing hole communicating with the outside and the wire insertion passage.

8. A medical treatment instrument comprising:
the basket catheter according to claim 1; and
an auxiliary treatment instrument inserted into the lumen of the inner tubular member.

9. The medical treatment instrument according to claim 8,
wherein the auxiliary treatment instrument is a balloon catheter, a micro-catheter, a forceps, a laser probe, a fiber scope, an electronic hydraulic lithotripsy probe or a guide wire.

10. A method for producing the basket catheter of claim 1, the method comprising:
preparing the elastic wires forming the expandable basket part, and the tubular connector connecting the inner tubular member and the elastic wires, and including wire insertion passages arranged in a circumferential direction;
inserting a proximal end part of the elastic wire into the wire insertion passage from a distal side;
joining the elastic wires and the tubular connector together, and
connecting the small-diameter portion of the tubular connector to the distal end of the inner tubular member so that the inner diameter of the small-diameter portion is the same as or larger than the inner diameter of the distal end of the inner tubular member.

11. The method for producing the basket catheter according to claim 10,
wherein the tubular connector includes on a peripheral wall of the tubular connector a fixing hole communicating with an outside and the wire insertion passage, and
a joining agent is injected into the fixing hole in the step of joining the elastic wires and the tubular connector together.

12. The method for producing the basket catheter according to claim 10, further comprising
reducing an outer diameter of the proximal end part of the elastic wire before inserting the elastic wire into the wire insertion passage.

13. The method for producing the basket catheter according to claim 10, further comprising:
preparing the inner tubular member by spirally winding a wire, so that the inner tubular member has a hollow coil body formed of the wire wound spirally; and
inserting a proximal end part of the tubular connector into a distal end part of a lumen of the inner tubular member.

* * * * *